United States Patent [19]

Fertel et al.

[11] Patent Number: 5,086,188
[45] Date of Patent: Feb. 4, 1992

[54] PREPARATION OF 3,5-DICHLOROPHTHALIC ACID AND 3,5-DICHLOROPHTHALIC ANHYDRIDE

[75] Inventors: Lawrence B. Fertel, Buffalo; Neil J. O'Reilly; Henry C. Lin, both of Grand Island, all of N.Y.

[73] Assignee: Occidental Chemical Corporation, Niagara Falls, N.Y.

[21] Appl. No.: 641,961

[22] Filed: Jan. 16, 1991

[51] Int. Cl.⁵ .................... C07D 307/77; C07C 51/06
[52] U.S. Cl. ...................... 549/246; 560/83; 562/480; 562/483
[58] Field of Search ............ 562/483; 549/246

[56] References Cited

U.S. PATENT DOCUMENTS 4,981,999  1/1991  O'Reilly et al. .................... 562/480

Primary Examiner—Jose G. Dees
Assistant Examiner—Vera C. Clarke
Attorney, Agent, or Firm—James F. Tao; John H. Engelmann

[57] ABSTRACT

Plychlorophthalimides, specifically, N-substituted tetrachlorophthalimides and N-substituted trichlorophthalimides may be treated with zinc and a base in aqueous soluction to yield, after acidification, the product 3,5-dichlorophthalic acid or salts thereof.

19 Claims, No Drawings

PREPARATION OF 3,5-DICHLOROPHTHALIC ACID AND 3,5-DICHLOROPHTHALIC ANHYDRIDE

BACKGROUND OF THE INVENTION

This invention relates to a method for the preparation of 3,5-dichlorophthalic acid or salt thereof or 3,5-dichlorophthalic anhydride from N-substituted tetrachlorophthalimides and trichlorophthalimides. 3,5-Dichlorophthalic acid is useful in the synthesis of plant growth regulators (U.S. Pat. Nos. 3,940,419 and 4,017,299). 3,5-Dichlorophthalic acid and phthalic anhydride may be prepared in poor yield by direct chlorination methods. For example, phthalic anhydride may be chlorinated to produce a mixture of chlorinated phthalic anhydrides. The products may be separated and, eventually, 3,5-dichlorophthalic anhydride may be obtained in low yield. Hydrolysis converts the anhydride to the acid.

O'Reilly, et. al. disclose in U.S. patent application, Ser. No. 07/439,227, now U.S. Pat. No. 4,981,999 that tetrachloro, trichloro or dichloro phthalic anhydrides may be treated with zinc and sodium hydroxide in aqueous solution in order to remove chlorines. The chlorines are removed in the order, the fifth position first, the fourth position second and the third position third. Thus, if two chlorines are removed from tetrachlorophthalic anhydride the product obtained, after acidification, is 3,6 dichlorophthalic acid. Similarly, if one chlorine is removed from 3,4,6-trichlorophthalic anhydride, the product is 3,6-dichlorophthalic acid. This process involves the removal of chlorine and not an isomerization. The numbering of the dichloro and the trichloro derivatives are different because under the standard system of nomenclature, the trichloro derivative is numbered so as to give the chlorines the lowest possible number.

SUMMARY OF THE INVENTION

Surprisingly it has now been found that polychlorophthalimides, specifically, N-substituted tetrachlorophthalimides and N-substituted trichlorophthalimides may be treated with zinc and a base in aqueous solution to yield, after acidification, the product 3,5-dichlorophthalic acid or salts thereof.

DETAILED DESCRIPTION OF THE INVENTION

N-substituted tetrachlorophthalimides and trichlorophthalimides react differently from the corresponding phthalic anhydrides. The phthalimides may be treated with zinc and a base in aqueous solution to form 3,5-dichlorophthalic acid.

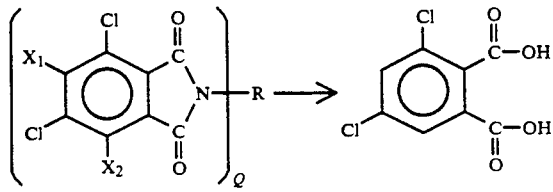

wherein $X_1$ and $X_2$ may be chlorine or hydrogen provided that both $X_1$ and $X_2$ may not be hydrogen and Q may be 1 or 2.

If Q=1, then R is a monovalent group. If Q=2, then R is a divalent group. More particularly, R may be a C1 to C8 straight or branched alkyl group, a C3 to C8 cycloalkyl group, or a C6 to C12 aryl group. The starting materials may be prepared by methods well known to those skilled in the art. For example, a monoamine or a diamine may be condensed with the desired polychlorophthalic anhydride in an appropriate solvent such as dioxane or acetic acid. They may be readily isolated by methods known to those skilled in the art.

The reaction is conducted in an aqueous solution. As the reaction begins, the polychlorophthalimide may not be fully soluble in water. However, as the reaction proceeds the chlorines are replaced by hydrogen, and the imide is hydrolyzed to form the salt of dichlorophthalic acid. At this point the reaction product is soluble in the water. If desired, water soluble organic solvents such as lower alcohols, dimethyl sulfoxide, dimethyl formamide, acetonitrile, and N-methylpyrrolidone may be added to enhance the solubility of polychlorophthalimide.

The reaction is conducted in the presence of zinc metal which should be present in at least stoichiometric amounts. One mole of zinc is required for the removal of each mole of chlorine. However, since zinc may be consumed at side reactions, it is preferable to have some excess of zinc present. Up to six equivalents of zinc is an appropriate amount. It is preferred that the zinc metal be present in a finely divided form in order to maximize its surface area and thus maximize the rate of reaction.

The reaction requires a strongly basic solution. The preferred bases are alkali metal hydroxides. Sodium hydroxide and potassium hydroxide are most preferred because they are both rather inexpensive. If sodium or potassium hydroxide are chosen, the concentration of base to be used is in the range from about 5% to about 25% based on the weight of the solvent. The optimal concentration of base is about 20%. In a typical reaction, the N-substituted phthalimide is added to a 20% alkali hydroxide solution in water, along with the zinc metal and optionally water miscible organic solvent. The preferred temperature range of the reaction is from about 60° to about 100° C. Lower temperatures decrease the reaction rate. Within the preferred temperature range, a temperature can be selected which allows the reaction to be completed within a reasonable period of time such as three to five hours.

The product of the reaction is the disodium salt of 3,5-dichlorophthalic acid. The reaction mixture also contains the amine or diamine which was used to prepare the starting phthalimide. In order to avoid difficulties, it is highly desirable to remove the amine by extracting with a solvent such as ether or ethyl acetate, or by some other means known to those skilled in the art. Once the amine has been removed, the desired 3,5-dichlorophthalic acid, or salts thereof, may be isolated by acidification by methods well known to those skilled in the art. If acidification is conducted carefully, so that the solution becomes neutral rather than becoming highly acidic, the mono salt of the 3,5-dichlorophthalic acid can be precipitated. The phthalic acid itself may be recovered from the salt by further acidification, by methods well known by those skilled in the art, and extraction with an organic solvent such as ethyl acetate.

The 3,5-dichlorophthalic acid may be readily converted to 3,5-dichlorophthalic anhydride by methods well known to those skilled in the art. For example, treatment of the acid with acetic anhydride readily converts the acid to the anhydride. Another method of converting the acid to the anhydride is to reflux the acid with a hydrocarbon such as xylene or toluene and use an appropriate trap to condense the water which vaporizes.

The following examples further illustrate this invention.

EXAMPLE 1

Preparation of 3,5-dichlorophthalic acid from Tetrachloro-N-phenylphthalimide

Tetrachloro-N-phenylphthalimide (30 grams) was added to 300 mL of 15% aqueous NaOH and 15 grams of zinc dust. The mixture was then heated to 65° C. and stirred at that temperature for 8 hours.

After cooling to room temperature, the reaction mixture was filtered and the filter cake washed with 100 mL of water. The water layer was then extracted with 2×100 mL of dichloromethane. Addition of conc. HCl to a pH of 1.0 led to a precipitate which was extracted into ethyl acetate. The ethyl acetate solution was dried over magnesium sulfate. Removal of the solvent and subsequent drying in a vacuum desiccator (80° C., 0.5 mmHg) led to 3,5-dichlorophthalic acid (18.92 g, 96.8%, purity 80% by GC). A sample was recrystallized from water to give a product with a mp of 171°–172° C.

EXAMPLE 2

Preparation of 3,5-dichlorophthalic acid from Tetrachloro-N-methylphthalimide

A mixture of 1.0 gram of tetrachloro-N-methylphthalimide, 0.7 grams of zinc dust and 10 mL of 20% aqueous NaOH Was combined and stirred at 65° C. for 3 hours. A sample of the reaction mixture was shown to contain 41.62% 3,5-dichlorophthalic acid.

EXAMPLE 3

Preparation of 3,5-dichlorophthalic acid from N-N'-dimethylene bis (tetrachlorophthalimide)

A mixture of 0.5 grams of N-N'-dimethylene bis(tetrachlorophthalimide), 0.27 grams of zinc dust, and 5 mL of aqueous 10% NaOH was combined and heated at 60° C. for 48 hours. An assay of the reaction mixture showed 39% 3,5-dichlorophthalic anhydride, identical in retention time to an authentic sample prepared above.

EXAMPLE 4

Preparation of 3,5-dichlorophthalic acid from 3,4,6-trichloro N-phenylphthalimide A mixture of 1.0 gram of 3,4,6-trichloro-N-phenylphthalimide, 1.0 gram of zinc dust and 10 mL of 5% NaOH were combined and heated to 60° C. for 25 hours. Assay of the reaction mixture showed 36.7% formation of 3,5-dichlorophthalic acid.

COMPARATIVE EXAMPLE 1

Tetrachloro-N-phenylphthalimide was reacted with sodium formate in methanol containing a catalytic amount of palladium on carbon. Exclusive production of N-phenylphthalimide occurred. No partially chlorinated material could be seen.

What is claimed is:

1. A process for the preparation of salts of 3,5-dichlorophthalic acid which comprises reacting the polychlorophthalimide represented by the following formula

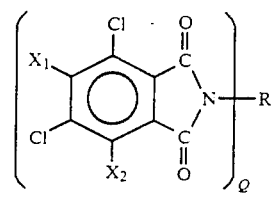

wherein $X_1$ and $X_2$ may be chlorine or hydrogen provided that both $X_1$ and $X_2$ may not be hydrogen, Q may be 1 or 2, and the R group may be a monovalent or divalent organic group selected from the group consisting of C1 to C8 straight or branched alkyl, C3 to C8 cycloalkyl, and C6 to C12 aryl; with metallic zinc in the presence of a base, whereby a reaction mixture containing a salt of 3,5-dichlorophthalic acid is formed.

2. A process according to claim 1 in which the base is selected from the group consisting of sodium hydroxide and potassium hydroxide.

3. A process according to claim 1 wherein in the temperature of the reaction is between 20° C. and 100° C.

4. A process according to claim 1 with the additional step of acidifying the reaction mixture.

5. A process according to claim 4 wherein the acidification is conducted to the neutral point whereby a monosodium salt of 3,5-dichlorophthalic acid is formed.

6. A process according to claim 4 wherein the acidification is sufficient to form 3,5-dichlorophthalic acid.

7. A process according to claim 1 wherein the polychlorophthalimide is 3,4,6-trichloro-N-methylphthalimide.

8. A process according to claim 1 wherein the polychlorophtha imide is 3,4,6-trichloro-N-phenylphthalimide.

9. A process according to claim 1 wherein said polychlorophthalimide is tetrachloro-N-methyl phthalimide.

10. A process according to claim 1 wherein said polychlorophthalimide is tetrachloro-N-phenyl phthalimide.

11. A process according to claim 4 wherein the polychlorophthalimide is 3,4,6-trichloro-N-methylphthalimide.

12. A process according to claim 4 wherein the polychlorophthalimide is 3,4,6-trichloro-N-phenylphthalimide.

13. A process according to claim 4 wherein said polychlorophthalimide is tetrachloro-N-methyl phthalimide.

14. A process according to claim 4 wherein said polychlorophthalimide is tetrachloro-N-phenyl phthalimide.

15. A process according to claim 6 with the additional step of dehydrating 3,5-dichlorophthalic acid to form 3,5-dichlorophthalic anhydride.

16. A process according to claim 15 wherein the polychlorophthalimide is 3,4,6-trichloro-N-methylphthalimide.

17. A process according to claim 15 wherein the polychlorophthalimide is 3,4,6-trichloro-N-phenylphthalimide.

18. A process according to claim 15 wherein said polychlorophthalimide is tetrachloro-N-methyl phthalimide.

19. A process according to claim 15 wherein said polychlorophthalimide is tetrachloro-N-phenyl phthalimide.

* * * * *